(12) United States Patent
Ozawa

(10) Patent No.: US 11,709,147 B2
(45) Date of Patent: Jul. 25, 2023

(54) ELECTROLYTE MEASURING DEVICE

(71) Applicant: Hitachi High-Tech Corporation, Tokyo (JP)

(72) Inventor: Satoshi Ozawa, Tokyo (JP)

(73) Assignee: HITACHI HIGH-TECH CORPORATION, Tokyo (JP)

(*) Notice: Subject to any disclaimer, the term of this patent is extended or adjusted under 35 U.S.C. 154(b) by 279 days.

(21) Appl. No.: 17/271,724

(22) PCT Filed: Sep. 2, 2019

(86) PCT No.: PCT/JP2019/034356
§ 371 (c)(1),
(2) Date: Feb. 26, 2021

(87) PCT Pub. No.: WO2020/066472
PCT Pub. Date: Apr. 2, 2020

(65) Prior Publication Data
US 2021/0318260 A1    Oct. 14, 2021

(30) Foreign Application Priority Data
Sep. 28, 2018    (JP) .................................. 2018-184540

(51) Int. Cl.
*G01N 27/333*    (2006.01)
*G01N 27/416*    (2006.01)
(Continued)

(52) U.S. Cl.
CPC ......... *G01N 27/333* (2013.01); *G01N 27/301* (2013.01); *G01N 27/4163* (2013.01); *G01N 27/401* (2013.01)

(58) Field of Classification Search
CPC ............... G01N 27/333; G01N 27/301; G01N 27/4163; G01N 27/401
See application file for complete search history.

(56) References Cited

U.S. PATENT DOCUMENTS 3,569,608 A * 3/1971 Ance .................... H02G 15/013
174/91
4,189,367 A    2/1980 Connery et al.
(Continued)

FOREIGN PATENT DOCUMENTS

| | | |
|---|---|---|
| CN | 105164526 A | 12/2015 |
| JP | H7159361 A | 6/1995 |

(Continued)

OTHER PUBLICATIONS

Office Action dated Oct. 31, 2022 in Chinese Application No. 201980055670.4.
(Continued)

*Primary Examiner* — Alexander S Noguerola
(74) *Attorney, Agent, or Firm* — Miles & Stockbridge, P.C.

(57) ABSTRACT

The present invention provides an electrolyte measuring device that makes it possible to detect failure in the device with a high degree of accuracy. The electrolyte measuring device has: an ion-selective electrode to which an ion solution including ions is supplied; a reference electrode; a measurement section to measure a potential difference between the ion-selective electrode and the reference electrode; and a current measurement section to measure an electric current flowing in the reference electrode.

12 Claims, 12 Drawing Sheets

(51) Int. Cl.
*G01N 27/30* (2006.01)
*G01N 27/401* (2006.01)

(56) References Cited

U.S. PATENT DOCUMENTS

| | | | |
|---|---|---|---|
| 4,360,415 A | | 11/1982 | Brezinski |
| 4,851,104 A | | 7/1989 | Connery et al. |
| 5,100,530 A | * | 3/1992 | Dorr ................ G01N 27/49 |
| | | | 204/406 |
| 6,353,323 B1 | | 3/2002 | Fuggle |
| 2004/0259264 A1 | | 12/2004 | Morita et al. |
| 2016/0054257 A1 | | 2/2016 | Ishige et al. |

FOREIGN PATENT DOCUMENTS

| | | |
|---|---|---|
| JP | H8211015 A | 8/1996 |
| JP | H11248677 A | 9/1999 |
| JP | 2014219246 A | 11/2014 |
| JP | 2015155894 A | 8/2015 |
| KR | 10-2014-0123790 A | 10/2014 |
| WO | 2003036285 A1 | 5/2003 |

OTHER PUBLICATIONS

Search Report dated Nov. 19, 2019 in International Application No. PCT/JP2019/034356.
Written Opnion dated Nov. 19, 2019 in International Application No. PCT/JP2019/034356.
International Preliminary Report on Patentability dated Jul. 1, 2020 in International Application No. PCT/JP2019/034356.
Search Report dated May 24, 2022 in European Application No. 19868022.5.

* cited by examiner

ELECTROLYTE MEASURING DEVICE

TECHNICAL FIELD

The present invention relates: to an electrolyte measuring device; in particular to an electrolyte measuring device for analyzing an electrolyte component in a sample in an automatic analyzer used for analyzing a living body.

BACKGROUND ART

An automatic analyzer is known as a device for analyzing a sample containing protein included in a specimen such as blood or urine. An electrolyte measuring device is mounted on such an automatic analyzer. The electrolyte measuring device is configured so as to analyze an electrolyte component such as sodium (Na), potassium (K), or chlorine (Cl) in a sample for example.

Most of such electrolyte measuring devices use a method called an ion-selective electrode method (ISE method). The ISE method measures an electrolyte concentration in a specimen by measuring a potential difference between an ion-selective electrode (ISE) and a reference electrode. The ion-selective electrode has an ion-sensitive membrane to generate a potential difference in response to an ionic component.

The potential fluctuates in accordance with an electrolyte concentration in a specimen. The reference electrode is configured so as to get in touch with a solution called a reference electrode liquid in order to maintain a reference potential. As the reference electrode liquid, a KCL solution of a high concentration is used for example.

Further, it is also possible to form a device of a flow cell type as an ion-selective electrode or a reference electrode in order to achieve a high throughput. In the device of a flow cell type, a flow channel for supplying a sample to be measured is provided inside a housing and a sensitive membrane is provided in contact with the flow channel.

AS methods for quantifying a concentration of an electrolyte contained in a biological sample (blood, particularly, serum, plasma, urine, etc.) in the field of clinical examination, a non-dilution method and a dilution method are known. The non-dilution method is a method of measuring a biological sample as it is without being diluted as a specimen. On the other hand, the dilution method is a method of: diluting a predetermined amount of biological sample with a predetermined amount of diluent liquid; and measuring a specimen liquid after the dilution (diluted biological sample) by using the ISE method or the like. The dilution method can achieve a high stability in the ISE method because a dose of a sample liquid is small, a concentration of coexisting substances such as a protein and a lipid in a measurement liquid is low, and the effect of dirt caused by the coexisting substances is small.

In an electrolyte measuring device for a biopsy, a measurement method that combines an ISE method by a flow cell type and a dilution method is currently the mainstream. A container called a dilution tank is used to dilute a sample. A diluted biological sample prepared in the dilution tank is: transferred to a flow cell type ion-selective electrode through a pipe; and measured. The sample is measured by alternately: dispensing an internal standard liquid and the diluted biological sample into the dilution tank; and transferring them to an ion-selective electrode. An extremely high measurement accuracy is required for the ISE method and various technological developments are being carried out in order to reduce measurement errors as much as possible (for example, refer to Patent Literature 1 and Patent Literature 2). Patent Literature 1 however: aims to evaluate the characteristics of an ion-selective electrode; and does not propose a configuration for detecting air bubbles mixed in a flow cell flow channel and failure including the presence or absence of a noise in an output signal. Further, Patent Literature 2: aims to measure an output of an ISFET type pH sensor of a current device type; and does not propose a configuration for detecting failure including air bubbles and a noise. In this way, at present, publicly known technologies do not yet take sufficient measures to detect failure in a device.

CITATION LIST

Patent Literature

Patent Literature 1: Japanese Unexamined Patent Application Publication No. 2014-219246
Patent Literature 2: Japanese Unexamined Patent Application Publication No. Hei 11-248677

SUMMARY OF INVENTION

Technical Problem

The present invention provides an electrolyte measuring device that can: detect various kinds of failure with a high degree of sensitivity; and encourage a user to take measures in the electrolyte measuring device to which an ISE method by a flow cell type is applied.

Solution to Problem

An electrolyte measuring device according to the present invention has: an ion-selective electrode to which an ion solution including ions is supplied; a reference electrode; a measurement section to measure a potential difference between the ion-selective electrode and the reference electrode; and a current measurement section to measure an electric current flowing in the reference electrode.

Advantageous Effects of Invention

According to an electrolyte measuring device of the present invention, it is possible to provide the electrolyte measuring device that can: detect various kinds of failure with a high degree of sensitivity; and encourage a user to take measures in the electrolyte measuring device to which an ISE method by a flow cell type is applied.

DESCRIPTION OF EMBODIMENTS

The present embodiments are hereunder explained in reference to attached drawings. In the attached drawings, functionally identical elements may sometimes be represented by an identical number. Note that, although the attached drawings show embodiments and implementation examples based on the principles of the present disclosure, those are for the understanding of the present disclosure and are by no means used for a limited interpretation of the present disclosure. The descriptions in the present description are only typical examples and do not limit the scope of claims or application examples in the present disclosure in any sense.

Although sufficiently detailed explanations are provided for those skilled in the art to execute the present disclosure in the present embodiments, it should be understood that: other implementations and forms are also possible; and it is possible to change a configuration and a structure and replace various elements without departing from the scope and spirit of the technical ideas in the present disclosure. The following descriptions therefore should not be construed in a limited way.

First Embodiment

Figure 1:
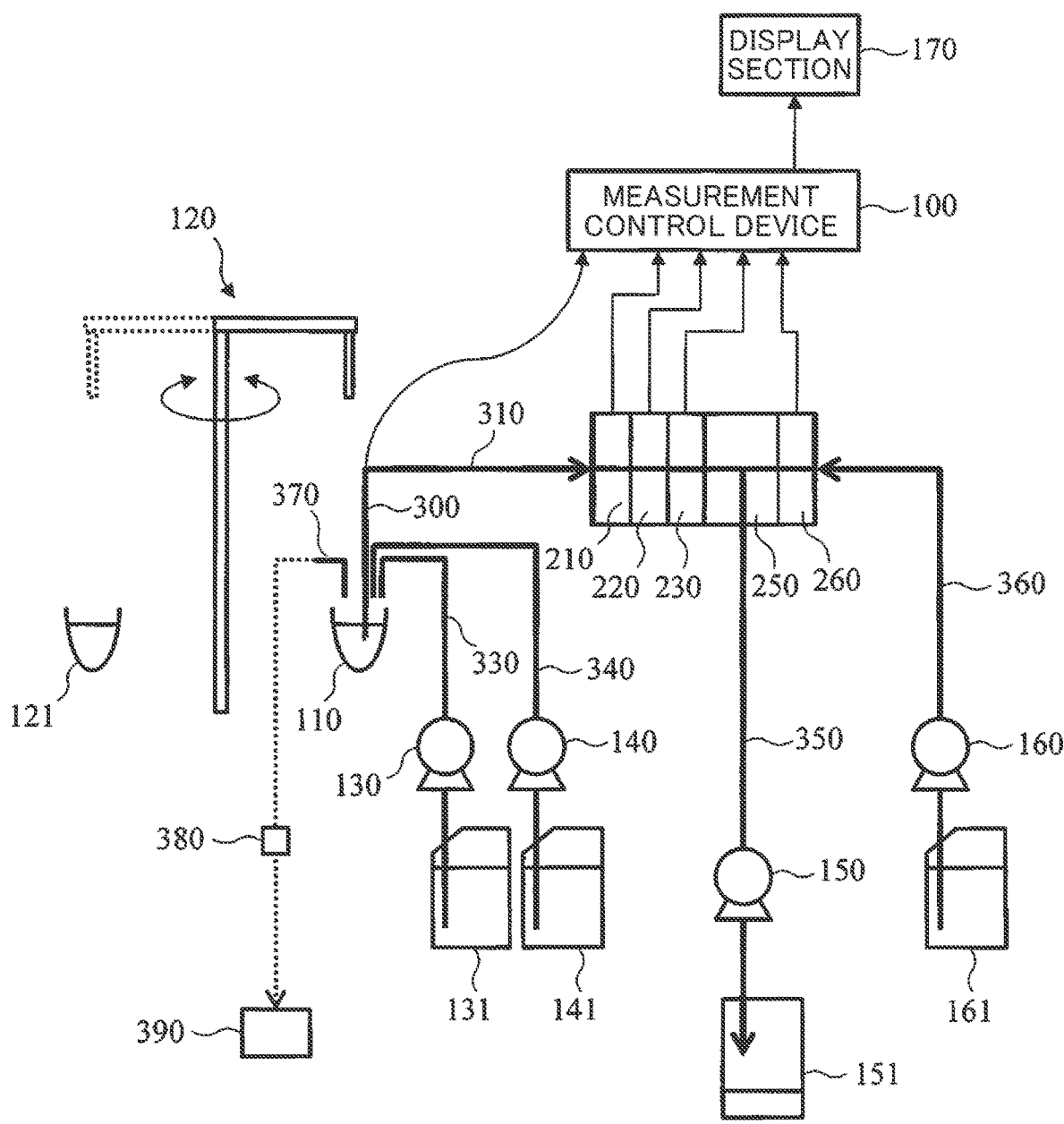
FIG. 1 is a schematic diagram showing a rough configuration of an electrolyte measuring device 10 according to a first embodiment.

FIG. 1 is a schematic diagram showing a rough configuration of an electrolyte measuring device 10 according to a first embodiment. The electrolyte measuring device 10: is an electrolyte measuring device equipped with an ion-selective electrode of a flow cell type; and has a measurement control device 100, a dilution tank 110, a specimen dispensing mechanism 120, a diluent liquid dispensing mechanism 130, an internal standard liquid dispensing mechanism 140, a liquid feeding mechanism 150, a reference electrode liquid feeding mechanism 160, a display section 170, a Cl-ion-selective electrode 210, a K-ion-selective electrode 220, an Na-ion-selective electrode 230, a liquid junction section 250, a reference electrode 260, a waste liquid nozzle 370, a drive mechanism for waste liquid nozzle (not shown in the figure), a waste liquid valve 380, and a waste liquid mechanism 390.

The measurement control device 100 functions as: a measurement section to manage measurement in the electrolyte measuring device 10; and a control section to manage various controls based on the results of the measurement. Further, the measurement control device 100 also functions as a display control section to control the display of the measurement results and the like at the display section 170. The display section 170 displays measurement results, warnings, and others in accordance with received data.

The dilution tank 110 is a container into which a diluted specimen liquid formed by mixing a specimen and a diluent liquid or an internal standard liquid is supplied. The diluted specimen liquid and the internal standard liquid are: alternately supplied into the dilution tank 110; and alternately measured accordingly. Here, in the present description, the diluted specimen liquid and the internal standard liquid may collectively be called "an ion solution" in some cases.

The specimen dispensing mechanism 120 has the function of sucking a specimen from a specimen container 121 and discharging the specimen into the dilution tank 110. The diluent liquid dispensing mechanism 130 is a device for dispensing a diluent liquid from a diluent liquid tank 131 to the dilution tank 110 through a diluent liquid dispensing pipe 330. The internal standard liquid dispensing mechanism 140 has the function of dispensing an internal standard liquid from an internal standard liquid tank 141 to the dilution tank 110 through an internal standard liquid dispensing pipe 340.

The liquid feeding mechanism 150 has the functions of: operating a pump to suck a diluted specimen liquid or an internal standard liquid from the dilution tank 110 toward the side of the ion-selective electrodes 210 to 230; and sucking the diluted specimen liquid or a reference electrode liquid from the liquid junction section 250 and the like and discarding the diluted specimen liquid or the reference electrode liquid to a waste liquid container 151 through a liquid feeding pipe 350. The reference electrode liquid feeding mechanism 160 is configured so as to: suck the reference electrode liquid from a reference electrode liquid tank 161; and transfer it to the reference electrode 260 through a reference electrode liquid feeding pipe 360.

A diluted specimen liquid or an internal standard liquid is supplied from the dilution tank 110 to the Cl-ion-selective electrode 210, the K-ion-selective electrode 220, and the Na-ion-selective electrode 230. On the other hand, a reference electrode liquid is supplied from the reference electrode liquid feeding mechanism 160 to the reference electrode 260. The liquid junction section 250 that serves as a passage of a diluted specimen liquid and a reagent in the flow cell type is provided at a position between the Cl-ion-selective electrode 210, the K-ion-selective electrode 220, or the Na-ion-selective electrode 230 and the reference electrode 260. The waste liquid mechanism 390 has the function of opening the waste liquid valve 380 and discarding the liquid through the waste liquid nozzle 370 when a liquid in the dilution tank 110 is discarded.

Figure 2:
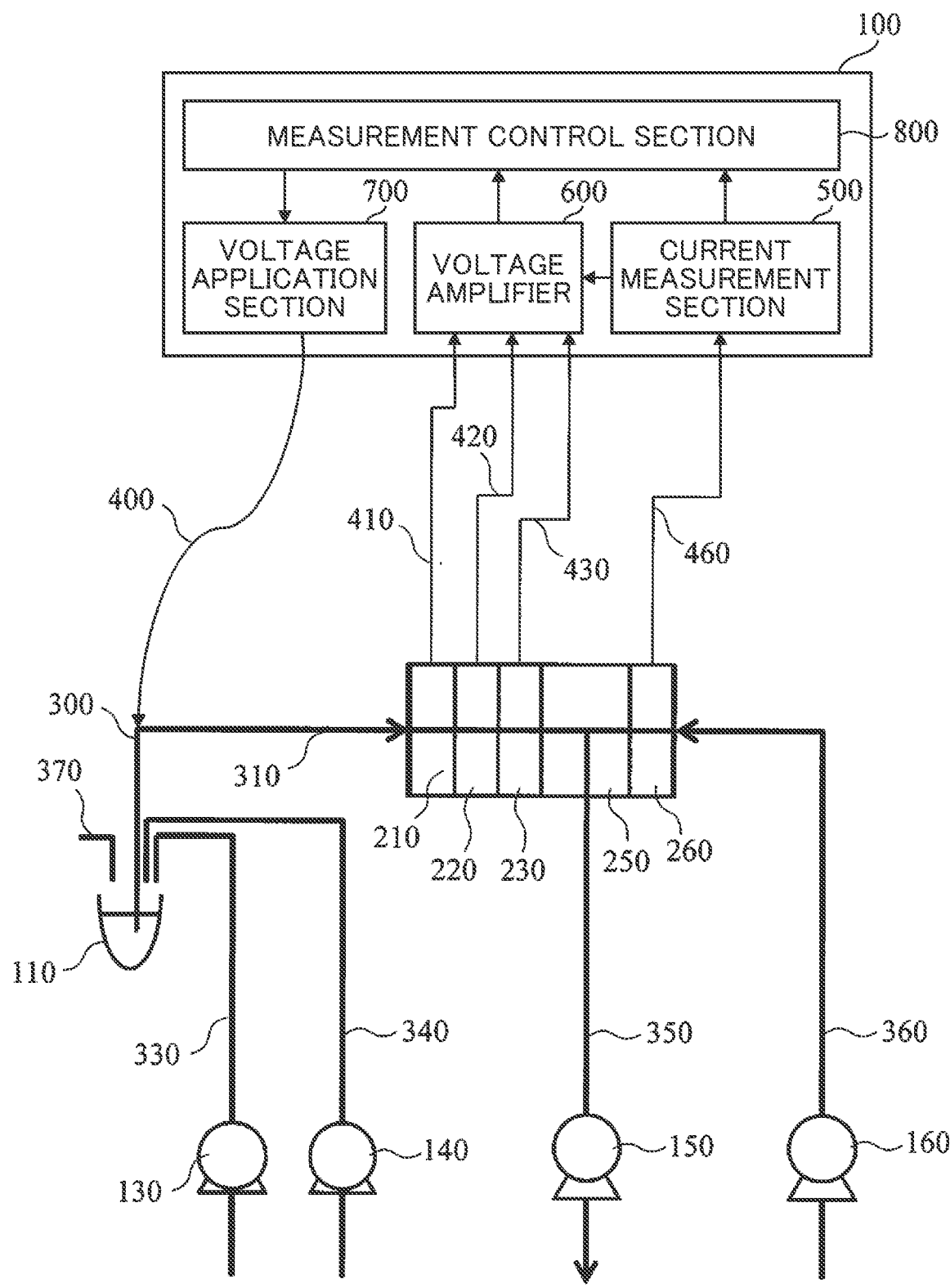
FIG. 2 is a schematic diagram showing a detailed configuration of a measurement control device 100 according to the first embodiment together with ambient constituent components.

FIG. 2 is a schematic diagram showing a detailed configuration of a measurement control device 100 together with ambient constituent components. The example shown in FIG. 2 is one of suitable configuration examples and it goes without saying that further additions and replacements to this configuration are possible. The measurement control device 100 in FIG. 2 has a current measurement section 500, a voltage amplifier 600, a voltage application section 700, and a measurement control section 800, as an example.

The current measurement section 500 is configured so as to: be connected to a reference electrode 260 through a shielded wire 460; and measure an electric current flowing in the reference electrode 260. The result of an electric current measured by the current measurement section 500 is used for detecting the presence or absence of air bubbles in a flow channel of a diluted specimen liquid or an internal standard liquid as it will be described later.

The voltage amplifier 600 is configured so as to amplify an output signal of the current measurement section 500. Further, the voltage amplifier 600: is connected to a Cl-ion-selective electrode 210, a K-ion-selective electrode 220, and an Na-ion-selective electrode 230 through shielded wires 410, 420, and 430; and has the function of amplifying the voltages of those electrodes 210 to 230.

The voltage application section 700: is connected to a wet contact member (or a wet contact electrode), for example a suction nozzle 300, existing on the upstream side of a flow cell flow channel from the ion-selective electrodes 210 to 230 through an electric wire 400; and applies a predetermined voltage to the suction nozzle 300. The voltage: is not applied during usual operation of measuring an ion concentration in a diluted specimen liquid or an internal standard liquid; and is applied when the presence or absence of failure in an electrolyte measuring device 10 is detected. In this first embodiment, the presence or absence of air bubbles in a flow channel of a diluted specimen liquid or an internal standard liquid is detected as an example of the presence or absence of failure.

When a diluted specimen liquid or an internal standard liquid is transferred from a dilution tank 110 to the ion-selective electrodes 210 to 230 or a reference electrode liquid is transferred from a reference electrode liquid tank 161 to the reference electrode 260 by a reference electrode liquid feeding mechanism 160, air bubbles that affect measurement may sometimes be mixed or generated in a flow channel during voltage measurement. When the sizes of the air bubbles are relatively large in comparison with the inner diameter of a flow cell flow channel, the electrical conductivity of the flow channel is hindered, an impedance increases, and noises are likely to be mixed.

when noises are extremely large, the output potentials of the ion-selective electrodes 210 to 230 fluctuate greatly. When the fluctuation width of the output potentials of the ion-selective electrodes 210 to 230 is larger than a standard value, it is possible to exclude the measurement result obtained from the output potentials as an error (false measurement) and encourage an operator to remeasure. When noises are relatively small however, it is not always easy to evaluate the reliability of a measured value only from the measurement results of the output potentials of the ion-selective electrodes 210 to 230.

In the first embodiment therefore, the voltage application section 700 apples a predetermined voltage to a member (for example, the suction nozzle 300) existing on the upstream side from the ion-selective electrodes 210 to 230 and, on that occasion, the current measurement section 500 measures an electric current flowing in the reference electrode 260. The presence or absence of air bubbles in the flow channel is determined by whether or not the electric current is larger than or equal to a threshold value. That is, in the first embodiment, the current measurement section 500 also judges the presence or absence of air bubbles in a flow channel by detecting the electric current of the reference electrode 260 while the presence or absence of false measurement is judged by detecting the fluctuation of the output potentials of the ion-selective electrodes 210 to 230. That is, the current measurement section 500 judges the presence or absence of air bubbles by comparing a measured electric current value with a threshold value. It is possible to use the result as an indicator of the reliability of measured values of the ion-selective electrodes 210 to 230 and as a judgment material for a warning or the necessity of remeasurement. According to the first embodiment therefore, failure in a device can be detected more accurately and a higher-precision measurement becomes possible. Note that, although the voltage application section 700 adopts the configuration of applying a voltage to the suction nozzle 300 that exists on the upstream side from the ion-selective electrodes 210 to 230 as an example in FIG. 2 and FIG. 3, instead of this, it is also possible to adopt a configuration of applying a voltage to the ion-selective electrodes 210 to 230.

The measurement control section 800: receives amplified signals of voltages of the ion-selective electrodes 210 to 230 from the voltage amplifier 600; and measures the voltages of the ion-selective electrodes 210 to 230 on the basis of the amplified signals. Further, the measurement control section 800 has the functions of: measuring an electric current value flowing in the reference electrode 260 on the basis of an output signal from the current measurement section 500; and controlling the voltage application section 700 and the like in accordance with the measured value. Furthermore, the measurement control section 800: measures an electric current value flowing in the reference electrode 260 on the basis of an output signal from the current measurement section 500; calculates a flow channel resistance of a flow cell flow channel (the suction nozzle 300 to the reference electrode 260 or the ion-selective electrodes 210 to 230 to the reference electrode) on the basis of the measured value; and further judges the presence or absence of air bubbles in the flow channel. In other words, the measurement control section 800 functions as a judgment section to judge the presence or absence of air bubbles in the flow channel of a diluted specimen liquid on the basis of the electric current value measured by the current measurement section 500.

Figure 3:
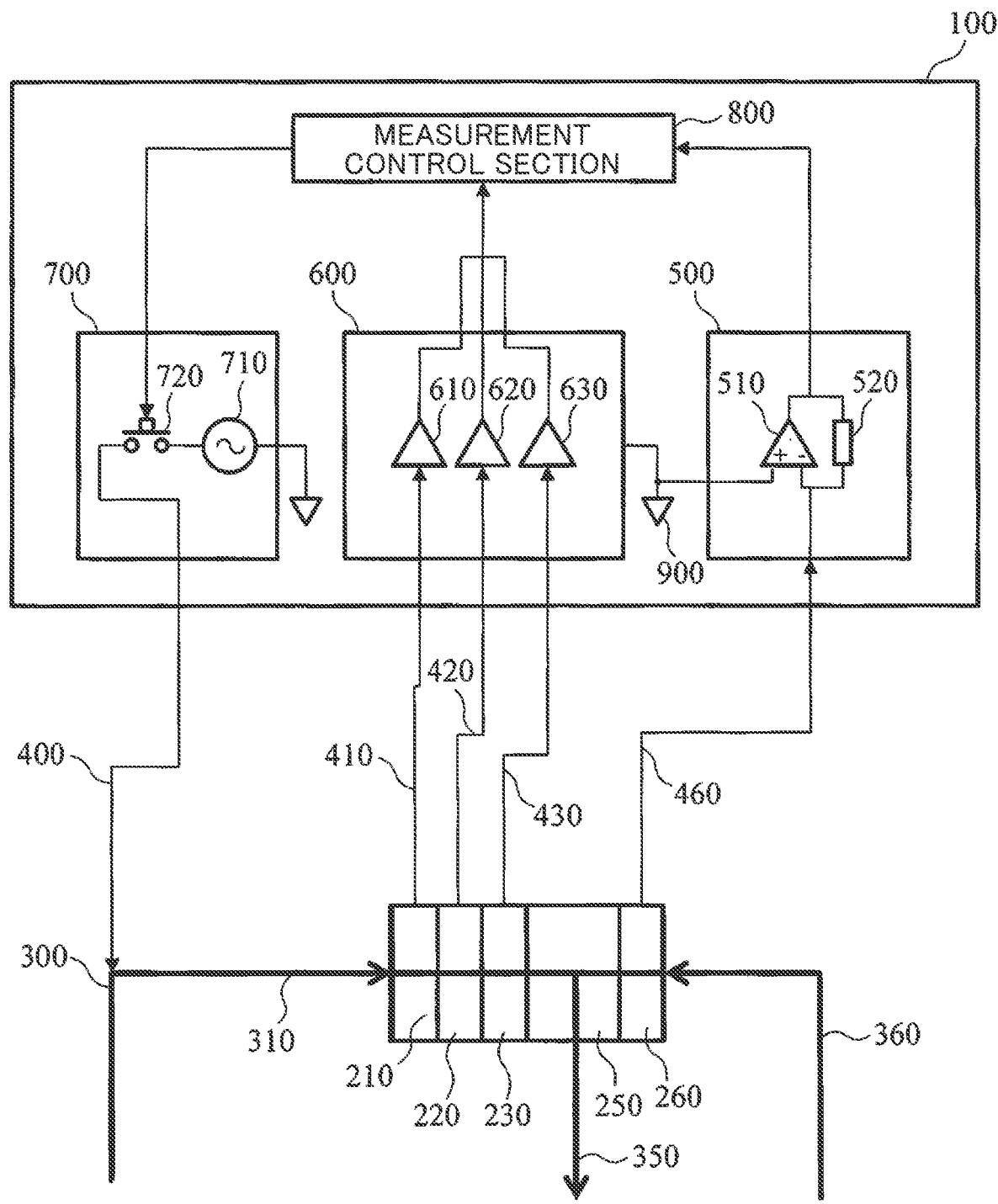
FIG. 3 is a circuit diagram explaining a configuration example of the measurement control device 100 according to the first embodiment further in detail.

A configuration example of a measurement control device 100 according to the first embodiment is explained further in detail in reference to the circuit diagram in FIG. 3. FIG. 3 is a circuit diagram explaining a configuration of a current measurement section 500, a voltage amplifier 600, and a voltage application section 700 further in detail.

The current measurement section 500: has an OP amplifier 510 and a feedback resistance 520 as an example; and can be configured as a type current-voltage conversion circuit based on the OP amplifier 510. In this example, an inverted input terminal (−) of the OP amplifier 510 is connected to an end of the resistance 520 and a shielded wire 460. The inverted input terminal: is an input terminal of the current measurement section 500; and is connected to an output terminal of a reference electrode 260.

On the other hand, a non-inverted input terminal (+) of the OP amplifier 510 is connected to a ground terminal (GND) 900 as a reference voltage terminal. An output terminal of the OP amplifier 510: is connected to the other end of the resistance 520; and is an output terminal of the current measurement section 500. As an example, it is possible to adopt AD549 as the OP amplifier 510 and a resistor of 1 GΩ as the feedback resistance 520 but the present invention is not limited to the example.

According to this configuration, the current measurement section 500: can convert an electric current flowing from the shielded wire 460 in the input terminal into a voltage with a conversion coefficient (sensitivity) of $-10^9$ (V/A) times; and can output the voltage from the output terminal. An output signal of the current measurement section 500 is: inputted to a measurement control section 800; and inputted to an AD converter (not shown in the figure) installed inside the measurement control section 800.

The voltage amplifier 600 is connected to the ground terminal 900 and has impedance conversion circuits 610, 620, and 630 comprising OP amplifiers. Input terminals of the impedance conversion circuits 610, 620, and 630 are respectively connected to the shielded wires 410, 420, and 430 stated earlier and output terminals are inputted to an AD converter (not shown in the figure) in the measurement control section 800 through a multiplexer that is not shown in the figure.

The voltage application section 700 has a power source 710 and an analog switch 720. The power source 710 is connected between a ground terminal and the analog switch 720 and the analog switch 720 is connected between a suction nozzle 300 and the power source 710 and configured so as to: switch between conductive state/non-conductive state; and switch supply/cutoff of power-supply voltage from the power source 710. ON/OFF of the switch 720 is switched by a control signal from the measurement control section 800. The switch 720 can be: in the conductive state (ON) when a flow channel resistance is measured and the detection of the presence or absence of air bubbles is operated in a flow cell flow channel; and in the non-conductive state (OFF) when ion concentrations of a diluted specimen liquid or an internal standard liquid are measured as usual and a natural electric current that will be explained after a second embodiment is measured.

Figure 4:
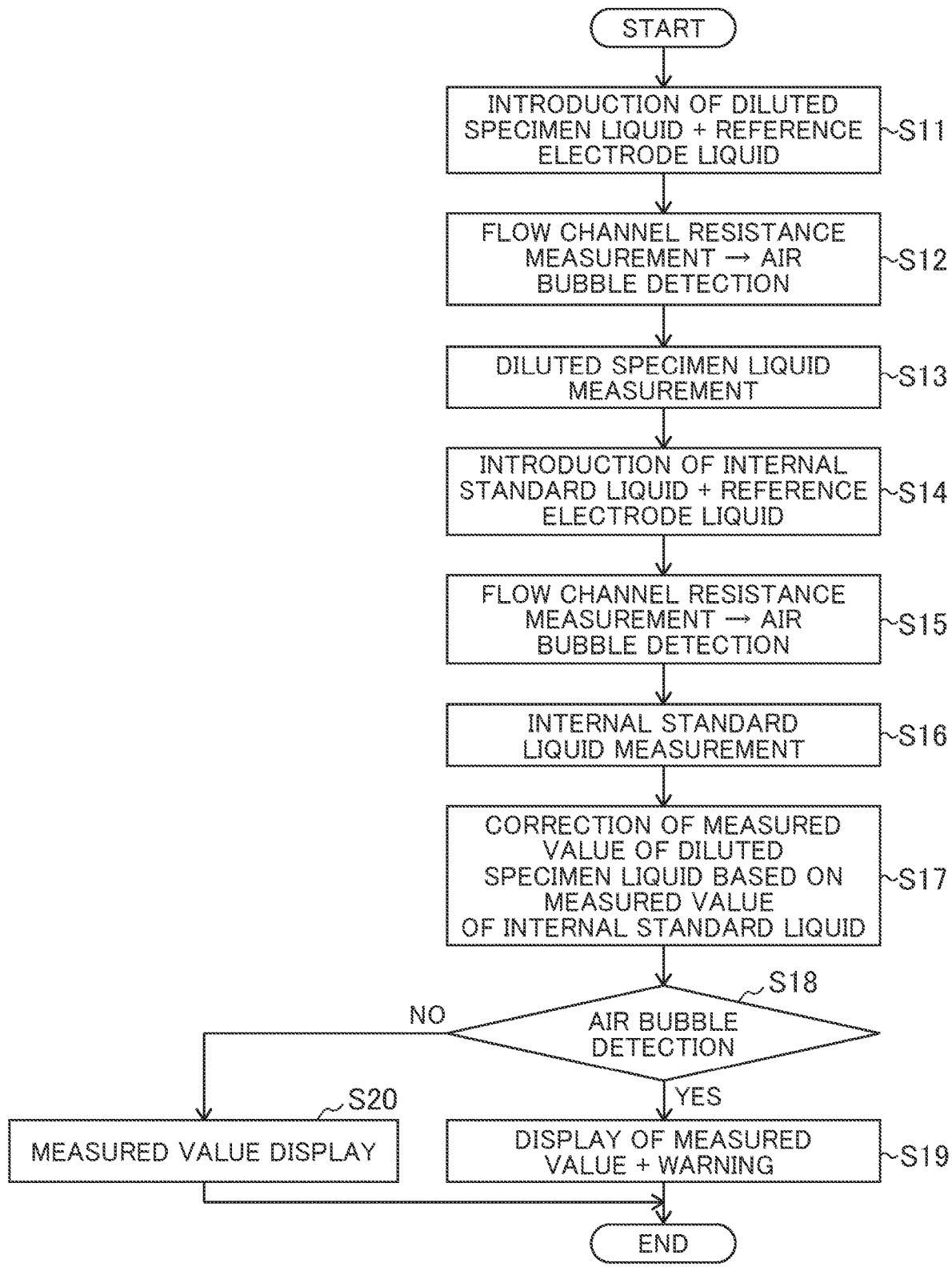
FIG. 4 is a flowchart explaining operations of the electrolyte measuring device 10 according to the first embodiment.

Operations of an electrolyte measuring device 10 according to the first embodiment are hereunder explained in accordance with the flowchart in FIG. 4. Note that the following sequence of transfer, waste, and others of various liquids is just an example and can appropriately be changed in the range where similar measurement is possible.

A specimen dispensed from a specimen container 121 to a dilution tank 110 by a specimen dispensing mechanism 120 is mixed with a diluent liquid supplied from a diluent liquid tank 131 by a diluent liquid dispensing mechanism 130 and a diluted specimen liquid is obtained. The diluted specimen liquid is transferred and wasted through a suction nozzle 300, a suction pipe 310, ion-selective electrodes 210, 220, and 230, a liquid junction section 250, and a liquid feeding pipe 350 by operation of a liquid feeding mechanism 150. Further, a reference electrode liquid is transferred to a reference electrode 260 and the liquid junction section 250 through a reference electrode liquid feeding pipe 360 by cooperative operation of a reference electrode liquid feeding mechanism 160 and the liquid feeding mechanism 150 (Step S11).

When a diluted specimen liquid touches a reference electrode liquid at the liquid junction section 250, a liquid junction is formed. When the liquid junction is formed, the ion-selective electrodes 210 to 230 output, as potential differences based on the potential of the reference electrode 260, output potentials corresponding to respective ion concentrations in the diluted specimen liquid. Since it takes time until the potential differences are stabilized, usually a measurement control device 100 measures the potential differences after a certain waiting time (Step S13).

The measurement control device 100: obtains potential differences between the ion-selective electrodes 210 to 230 and the reference electrode 260 in the measurement using the diluted specimen liquid; and obtains ion concentrations in the diluted specimen liquid from the measured values of the potential differences on the basis of the Nernst equation.

In the first embodiment, prior to the measurement of the ion concentrations, by a method described later, the presence or absence of air bubbles in a flow channel is detected as an example of failure of the device by measuring a resistance of the flow channel (Step S12).

Measurement using an internal standard liquid is also executed by procedures similar to the diluted specimen liquid. After the completion of the measurement of the diluted specimen liquid: the diluted specimen liquid remaining in the dilution tank 110 is discarded; an internal standard liquid is injected into the dilution tank 110 instead of this; and measurement using the internal standard liquid starts. The internal standard liquid is transferred to the flow channel of the ion-selective electrodes 210 to 230. The reference electrode liquid is also transferred toward the reference electrode 260 likewise. Then the potential differences between the potentials of the ion-selective electrodes 210 to 230 to which the internal standard liquid is given and the potential of the reference electrode 260 are measured by the similar procedure (Step S16). In the measurement using the internal standard liquid too, prior to the measurement, a similar air bubble detection operation is executed (Step S15). The measurement of the diluted specimen liquid and the measurement of the internal standard liquid like this are executed alternately. Measured values of the diluted specimen liquid are corrected on the basis of a measured value of the internal standard liquid (Step S17).

When air bubbles are detected in an air bubble detection operation executed prior to the measurement of the diluted specimen liquid or the internal standard liquid (Yes at Step S18), the measurement results of ion concentrations are displayed and also warning information showing that air bubbles are detected is displayed on a display section 170 (Step S19) and this encourages an operator to consider various measures (remeasurement, maintenance, component replacement, repair, and others). When air bubbles are not detected (NO at Step S18), only measured values are displayed on the display section 170 as usual (Step S20). As the measured values, the measured values after correction at Step S17 are displayed. Note that, if it is judged that an obvious abnormality occurs, for example, a measurement result of a flow channel resistance exceeds a measurable range, the measurement control device 100 (regardless of an input by an operator) can also execute remeasurement automatically.

Flow channel resistance measurement and air bubble detection operation based on that in the first embodiment are hereunder explained. As stated earlier, in the first embodiment, the following flow channel resistance measurement and air bubble detection are executed after a diluted specimen liquid and a reference electrode liquid are transferred to a liquid junction section 250 and a liquid junction is formed before potential differences are measured by ion-selective electrodes 210 to 230. Specifically, an analog switch 720 in a voltage application section 700 is turned on in accordance with a control signal from a measurement control section 800. As a result, a voltage (for example, 0.1 V) based on a ground terminal 900 is applied from a power source 710 to a suction nozzle 300 through an electric wire 400.

When a flow channel from the suction nozzle 300 to a suction pipe 310, the ion-selective electrodes 210, 220, and 230, the liquid junction section 250, and the reference electrode 260 is completely filled with a diluted specimen liquid or an internal standard liquid and air bubbles do not exist in the flow channel, the output voltage of a current measurement section 500 becomes around 5 V as an example. On the other hand, when air bubbles of about 1 μL in volume get mixed in at any position in the flow channel, the output of the current measurement section 500 takes a value very lower than usual (for example, about 5 mV or lower).

The values of electric currents flowing in the current measurement section 500 are about 5 nA and about 5 pA or lower respectively when air bubbles do not exit and air bubbles exist as a result of conversion by the sensitivity ($10^9$ V/A) of the current measurement section 500. The flow channel resistances between the suction nozzle 300 and the reference electrode 260 are calculated as about 20 MΩ and about 20 GΩ or more respectively when air bubbles do not exit and air bubbles exist from the voltage (for example, 0.1 V) applied by the voltage application section 700.

In this way, a flow channel resistance obtained by dividing an applied voltage from the voltage application section 700 by a measured electric current value at the current measurement section 500 differs by about 3 digits or more depending on whether there are no air bubbles or not. In other words, it is possible to determine the presence or absence of air bubbles by setting an appropriate threshold value Rth between resistance values that differ by 3 digits or more. As a standard threshold value Rth, it is possible to adopt a mean value of the two values in a logarithmic scale, namely about 630 MΩ.

When the flow channel resistance is about 20 MΩ, it is judged that the flow channel resistance is less than the threshold value Rth and there are no air bubbles. Inversely when the flow channel resistance is about 20 GΩ, it is judged that air bubbles exist because the flow channel resistance is the threshold value Rth or more. Otherwise, by setting a plurality of threshold values between the 3-digit-different resistance values, it is possible to judge the presence or absence of air bubbles with a high degree of sensitivity or reliability. When sensitivity is prioritized, a threshold value is set to a lower value Rthl (for example, 200 MΩ) and, when it is judged that a flow channel resistance slightly exceeds the lower threshold value Rthl, it can be judged that there are relatively small air bubbles in the flow channel. When reliability is prioritized, it is possible to set a higher threshold value Rthh (for example, 2 GΩ). By setting a higher threshold value Rthh, it is possible to effectively eliminate the risk of being judged as positive (false positive) even though it is not positive due to disturbance such as noise.

Meanwhile, although the air bubble detection operation based on the measurement result of a flow channel resistance has been explained as being executed during both the measurement of a diluted specimen liquid and the measurement of an internal standard liquid in the above examples, the present invention is not limited to this. For example, it is also possible to execute the air bubble detection operation only during either of the measurement of a diluted specimen liquid and the measurement of an internal standard liquid.

As explained above, in an electrolyte measuring device 10 according to the first embodiment, a flow channel resistance in a flow channel of a flow cell is calculated on the basis of an electric current flowing in a reference electrode 260 and the presence or absence of air bubbles in the flow channel is judged by the calculation result. When air bubbles are detected, an operator is notified of the result. The operator can take various measures against the generation of air bubbles by the notification and hence the operator can measure ion concentrations in a diluted specimen liquid with a high degree of accuracy as a result.

Note that a conventional electrolyte measuring device does not have a current measurement section 500 and a voltage application section 700 in FIG. 3 and a shielded wire 460 is connected to a ground terminal 900. On the other hand, the first embodiment has a current measurement section 500 and a non-inverted input terminal (+) of an OP amplifier 510 is connected to a ground terminal 900. By a virtual short function of the OP amplifier 510, the potentials of an inverted input terminal (−) and the non-inverted input terminal (+) are kept the same. The voltage of the input terminal (inverted input terminal) in the current measurement section 500 in FIG. 3 therefore is the same as the ground terminal 900. In other words, in a current measurement section 500 according to the present embodiment, an output terminal of a reference electrode 260 is substantially maintained at a ground potential and ordinary measurement can be executed similarly to a conventional device. In other words, it can be said that a current measurement section 500 according to the present embodiment can easily be added to a conventional device and has a high upward compatibility with a conventional device.

MODIFIED EXAMPLE

Figure 5:
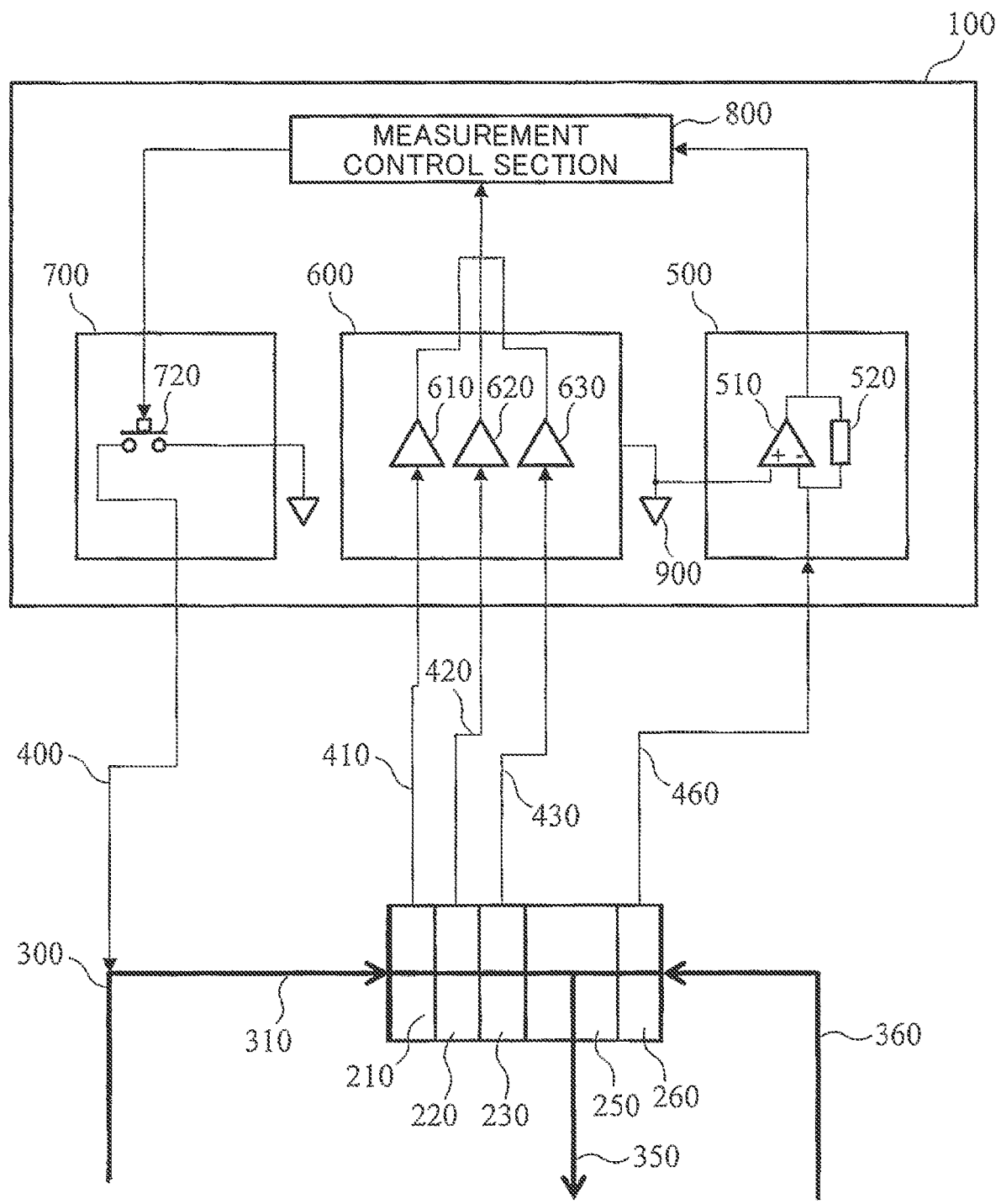
FIG. 5 is a schematic diagram showing a modified example according to the first embodiment.

An example modified from the first embodiment is shown in FIG. 5. In the modified example, a power source 710 in a voltage application section 700 is excluded and an analog switch 720 is directly connected to a ground terminal 900. In general, an interface potential exists between a metal and a solution or an electrode and a solution. When the interface potential is sufficiently large, that can be used as a substitute for a power source 710. In the modified example, since the configuration is simpler than the first embodiment, it is possible to reduce the cost, simplify the maintenance, and reduce the risk of failure.

Second Embodiment

Figure 6:
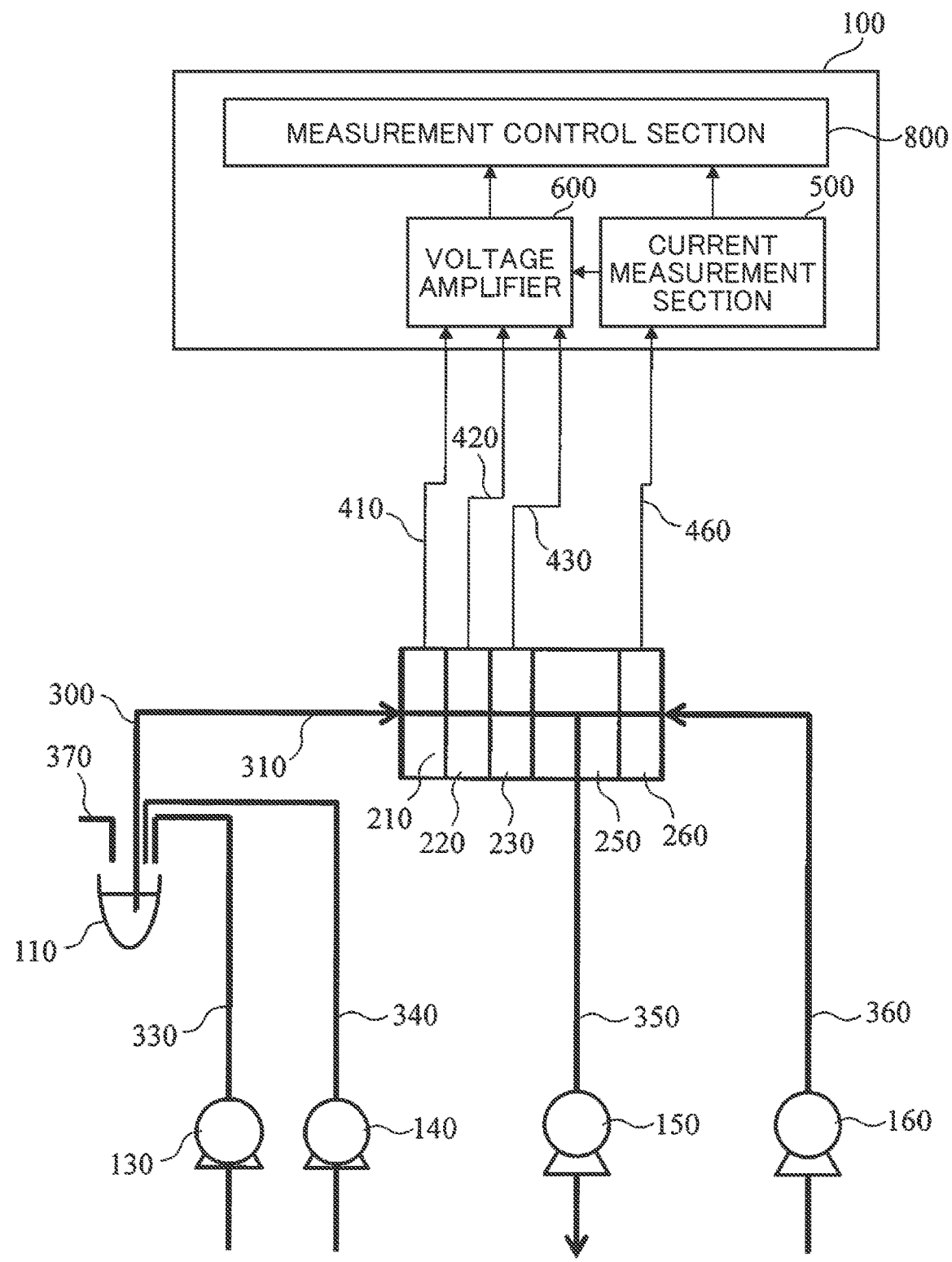
FIG. 6 is a schematic diagram showing a detailed configuration of a measurement control device 100 according to a second embodiment together with ambient constituent components.
Figure 7:
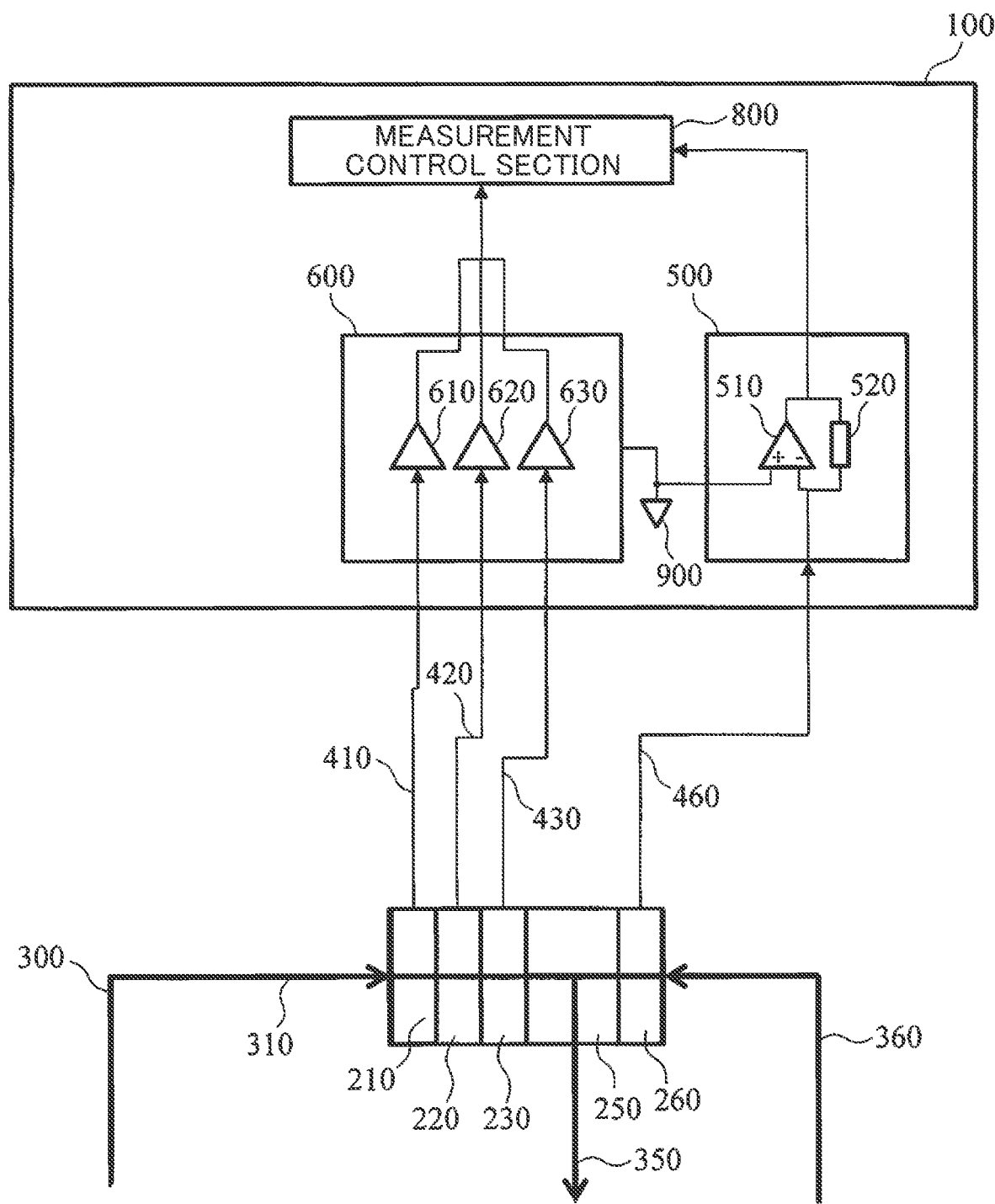
FIG. 7 is a circuit diagram explaining a configuration example of the measurement control device 100 according to the second embodiment further in detail.

An electrolyte measuring device according to a second embodiment is hereunder explained in reference to FIG. 6 and FIG. 7. In the second embodiment, the overall configuration (FIG. 1) is the same as the first embodiment. In the second embodiment, the configuration of a measurement control device 100 is different from the first embodiment.
[0050]
The details of the configuration of the measurement control device 100 according to the second embodiment are explained in reference to FIG. 6 and FIG. 7. To a component in FIG. 6 and FIG. 7 identical to a component in a measurement control device 100 according to the first embodiment, a reference code identical to a reference code in FIG. 2 and FIG. 3 is given and a duplicated explanation is omitted hereunder.

An electrolyte measuring device according to the second embodiment measures an electric current (hereunder referred to as a "natural electric current") flowing steadily in a reference electrode 260, instead of detecting the presence or absence of air bubbles in a flow channel of a flow cell, as an indicator of failure of the device during the measurement of a diluted specimen liquid. A measurement control device 100 according to the second embodiment therefore, unlike the first embodiment, excludes a voltage application section 700 and an electric wire 400 and has only a current measurement section 500 and a voltage amplifier 600. In the measurement of a diluted specimen liquid, it is possible to judge the magnitude of a natural electric current by measuring an electric current flowing in a reference electrode 260 where usually no electric current is assumed to flow by the current measurement section 500. The current measurement section 500 according to the second embodiment judges a degree of noise by comparing a measured electric current value with a threshold value. The result is used as: an indicator of reliability in measured values of ion-selective electrodes 210 to 230; and a material for determining the necessity of a warning and remeasurement.

A natural electric current is measured in a prototype of the configuration shown in FIG. 7 and a randomized baseline noise with an average of about 0 pA and an RMS (Root Mean Square) of about 0.01 pA is observed. When the device 10 is stopped, the noise level is nearly halved. Inversely, when the device 10 is operated, the noise level is nearly doubled. Further, besides the baseline noise, spike-like signals are also observed frequently. Spike-like signals with peak height absolute values of 0.1 pA or more are observed 86 times during a 40-minute measurement period and the difference between the maximum value and the minimum value during the period is about 2 µApp. Furthermore, a spike-like signal (natural electric current) with a peak height of about 0.1 µA synchronizing with the operation cycle of the device 10 is also observed.

Such a natural electric current is thought to be an electric current or an electric charge that: is mixed inside a pipe from a suction nozzle 300, a suction pipe 310, ion-selective electrodes 210, 220, and 230, a liquid junction section 250, a liquid feeding pipe 350, a liquid feeding mechanism 150, a reference electrode liquid feeding pipe 360, a reference electrode liquid feeding mechanism 160, and the like; and flows in the current measurement section 500 through a reference electrode 260 and a shielded wire 460.

Apart of an electric current or charge component is converted into a voltage component by a pipe resistance and the like and affects potential difference measurement of the ion-selective electrodes but, on the other hand, another part does not appear or hardly appears in the potential difference of the ion-selective electrodes. The former was discussed a lot in the past as noise, potential fluctuation, and others in potential difference measurement of the conventional ion-selective electrodes. Regarding the latter however, there is no conventional knowledge and it was not sufficiently studied in the past. By providing a current measurement section 500 to measure an electric current flowing in a reference electrode 260 separately from a measurement device of ion-selective electrodes like the present embodiment, such an electric current or charge component has become observable for the first time. Such an electric current or charge component as stated above has not yet been able to be measured in a conventional flow cell type electrolyte measuring device having only a device of observing a potential difference of ion-selective electrodes.

By using such a randomized baseline noise component and a spike-like peak in an electric current as clues, it is possible to trace various error factors including various disturbances such as vibration, electricity leakage, poor connection, temperature fluctuation, sample liquid flow, static electricity, electromagnetic waves, induced noise, induced electric current, and the like, state change inside a device, and the like.

Further, it is also possible to: isolate and identify error factors by using the electric current as an indicator and optimizing conditions; and take measures. Furthermore, the measurement of a natural electric current can be executed immediately before the measurement of a diluted specimen liquid or an internal standard liquid similarly to the air bubble detection operation in the first embodiment.

Third Embodiment

Figure 8:
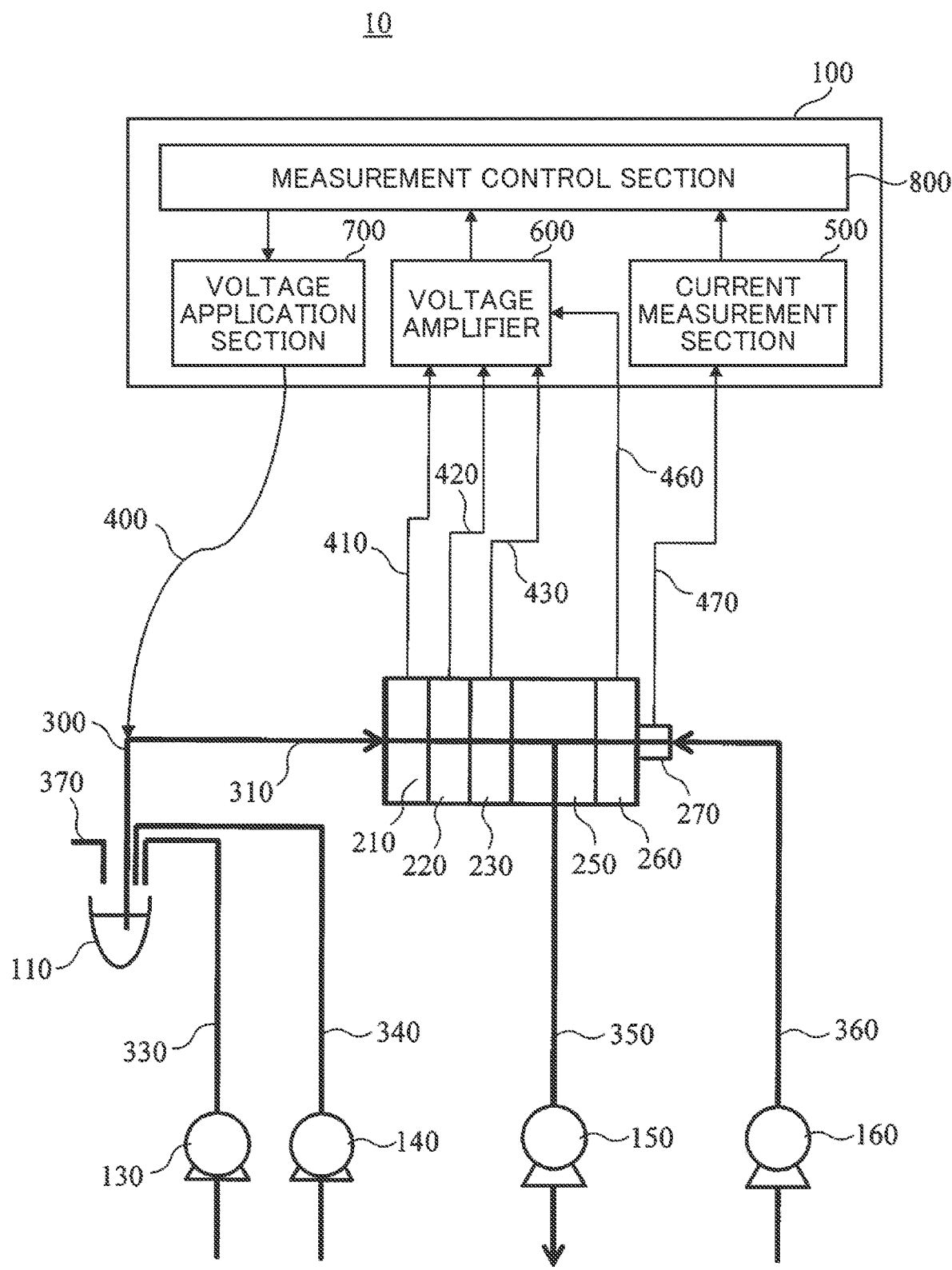
FIG. 8 is a schematic diagram showing a detailed configuration of a measurement control device 100 according to a third embodiment together with ambient constituent components.
Figure 9:
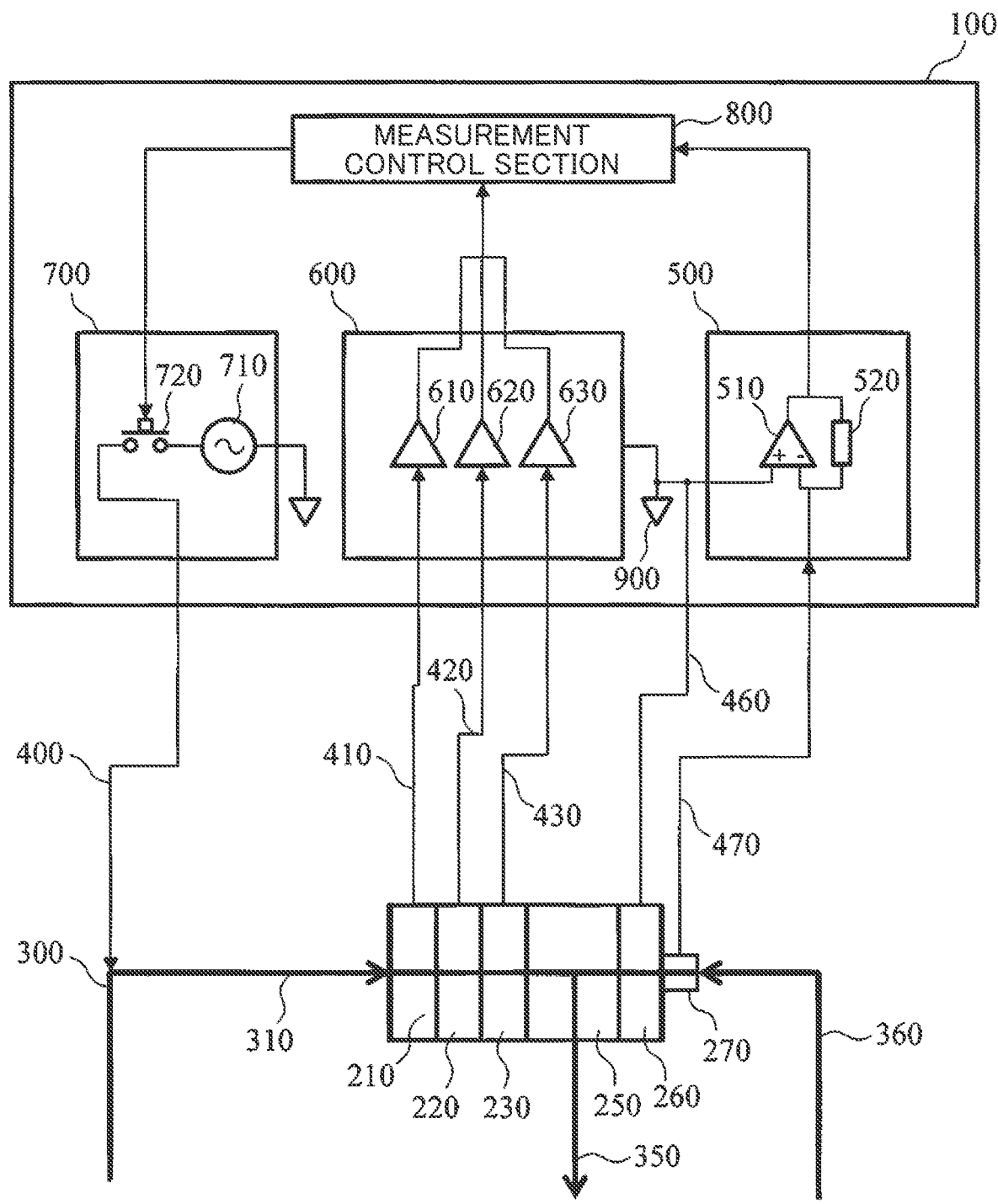
FIG. 9 is a circuit diagram explaining a configuration example of the measurement control device 100 according to the third embodiment further in detail.

An electrolyte measuring device according to a third embodiment is hereunder explained in reference to FIG. 8 and FIG. 9. In the third embodiment, the overall configuration (FIG. 1) is the same as the first embodiment. Further, the third embodiment also has a voltage application section 700 for detecting the flow channel resistance and the presence or absence of air bubbles in a flow cell flow channel similarly to the first embodiment.

In the third embodiment however, as shown in FIG. 8, an input terminal of a current measurement section 500 is connected to an electrode 270 through a shielded wire 470. The electrode 270 is an electrode different from a reference electrode 260 and is electrically connected to the rear surface of the electrode 270 on the side opposite to ion-selective electrodes 210 to 230 and a liquid junction section 250. As a material of the electrode 270, platinum (Pt) that is resistant to corrosion is preferably used.

More specifically, as shown in FIG. 9, an electric wire 470 is connected to an inverted input terminal of an OP amplifier 510, which is different from the first embodiment in which a shielded wire 460 extending from a reference electrode 260 is connected to an input terminal of a current measurement section 500. Note that a shielded wire 460 in the third embodiment is connected to a ground terminal 900 and a non-inverted input terminal of the OP amplifier 510 as shown in FIG. 9.

A flow channel of a flow cell is formed inside the electrode 270 and platinum (Pt), which is a material, is provided facing the flow channel. Further, electrical connection is secured between the platinum (Pt) and the electric wire 470.

The operation of the electrolyte measuring device according to the third embodiment: is nearly the same as the first embodiment; but is different from the first embodiment on the point that the electrode targeted for electric current detection is not the reference electrode 260 but the electrode 270 touching the rear surface of the reference electrode 260. Further, the point that a section for measuring a flow channel resistance is not from a suction nozzle 300 to the reference electrode 260 but from a suction nozzle 300 to the electrode 270 on the downstream side from the reference electrode 260 is also different from the first embodiment.

The effects of the third embodiment are nearly the same as those of the first embodiment. Since an electric current from the voltage application section 700 does not pass through the reference electrode 260 however, there is no risk of polarization or damage to an internal electrode. It is therefore possible to measure a flow channel resistance of a flow cell while taking time at a relatively high voltage from the voltage application section 700. Further, the flow channel of the flow cell where a flow channel resistance is measured is longer than that of the first embodiment by the length of the electrode 270. It is also possible therefore to detect air bubbles near the entrance of the reference electrode 260. Note that the material of the electrode 270 is preferably but not necessarily platinum and can be another metal of a high corrosion resistance, various conductive materials, an ion exchange resin, or the like.

The position where the electrode 270 is placed: is also not limited to a plane on the downstream side of a flow channel from the reference electrode 260; and may be any place in a reference electrode liquid feeding pipe 360, any place in a liquid feeding pipe 350, or the like, for example.

Note that a target for connecting an electric wire 400 is also not limited to the suction nozzle 300. For example, it is also possible to: provide an electrode similar to the electrode 270 at an arbitrary position in a suction pipe 310; and connect the electric wire 400 to the electrode.

Furthermore, it is also possible to detect the presence or absence of air bubbles in a diluent liquid dispensing pipe 330 by providing two electrodes in the diluent liquid dispensing pipe 330, connecting the voltage application section 700 to one electrode through an electric wire, and connecting the current measurement section 500 to the other electrode through another electric wire. It is also possible to adopt a nearly similar configuration to an internal standard liquid dispensing pipe 340.

The form of electric wire connection is also not limited to the form shown in FIG. 6. It is acceptable as long as, in two electrodes, one electrode is connected to the voltage application section 700 and the other electrode is connected to the current measurement section 500 and a connection method of exchanging connection destinations is as a matter of course included in the scope of the present invention.

Fourth Embodiment

Figure 10:
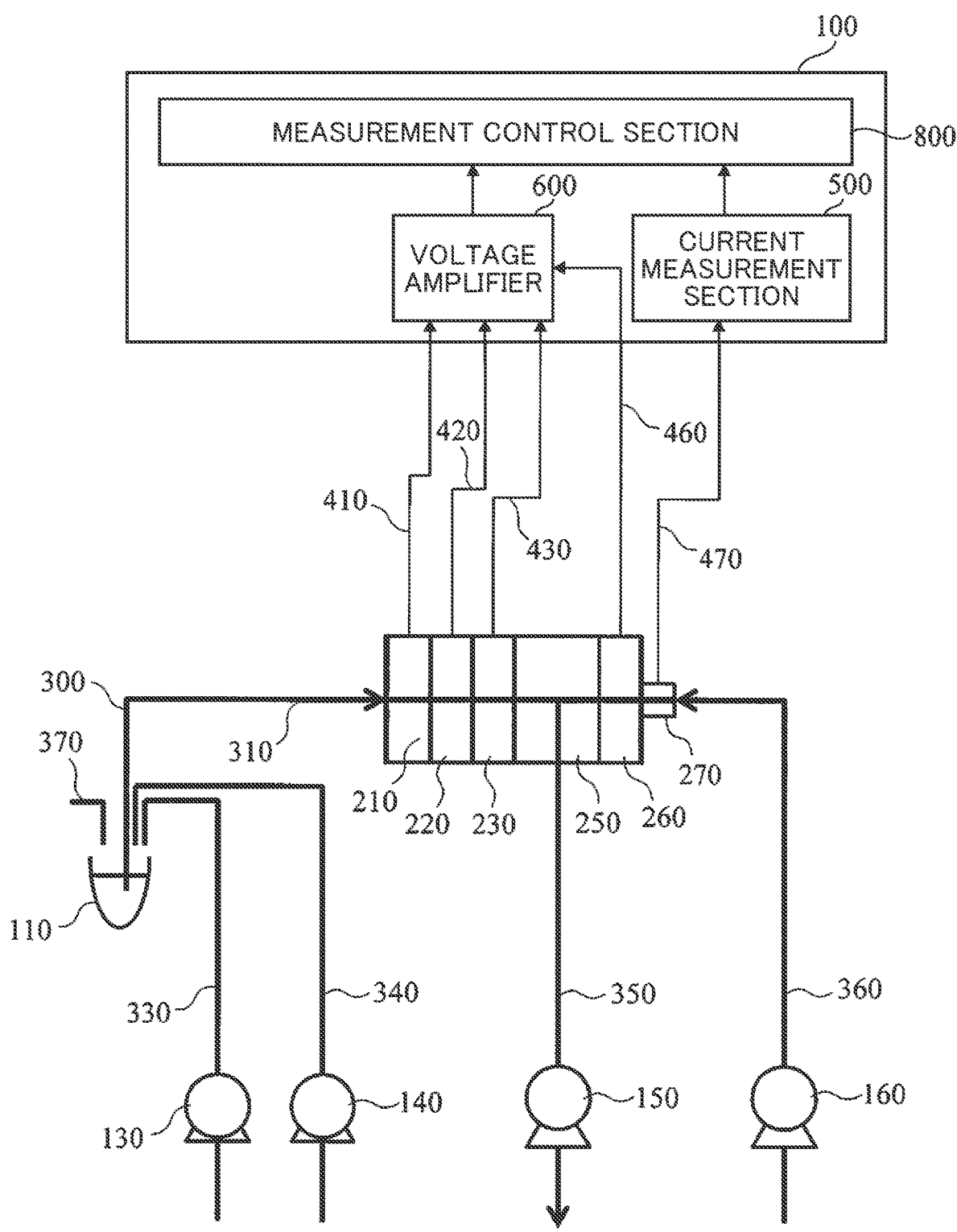
FIG. 10 is a schematic diagram showing a detailed configuration of a measurement control device 100 according to a fourth embodiment together with ambient constituent components.
Figure 11:
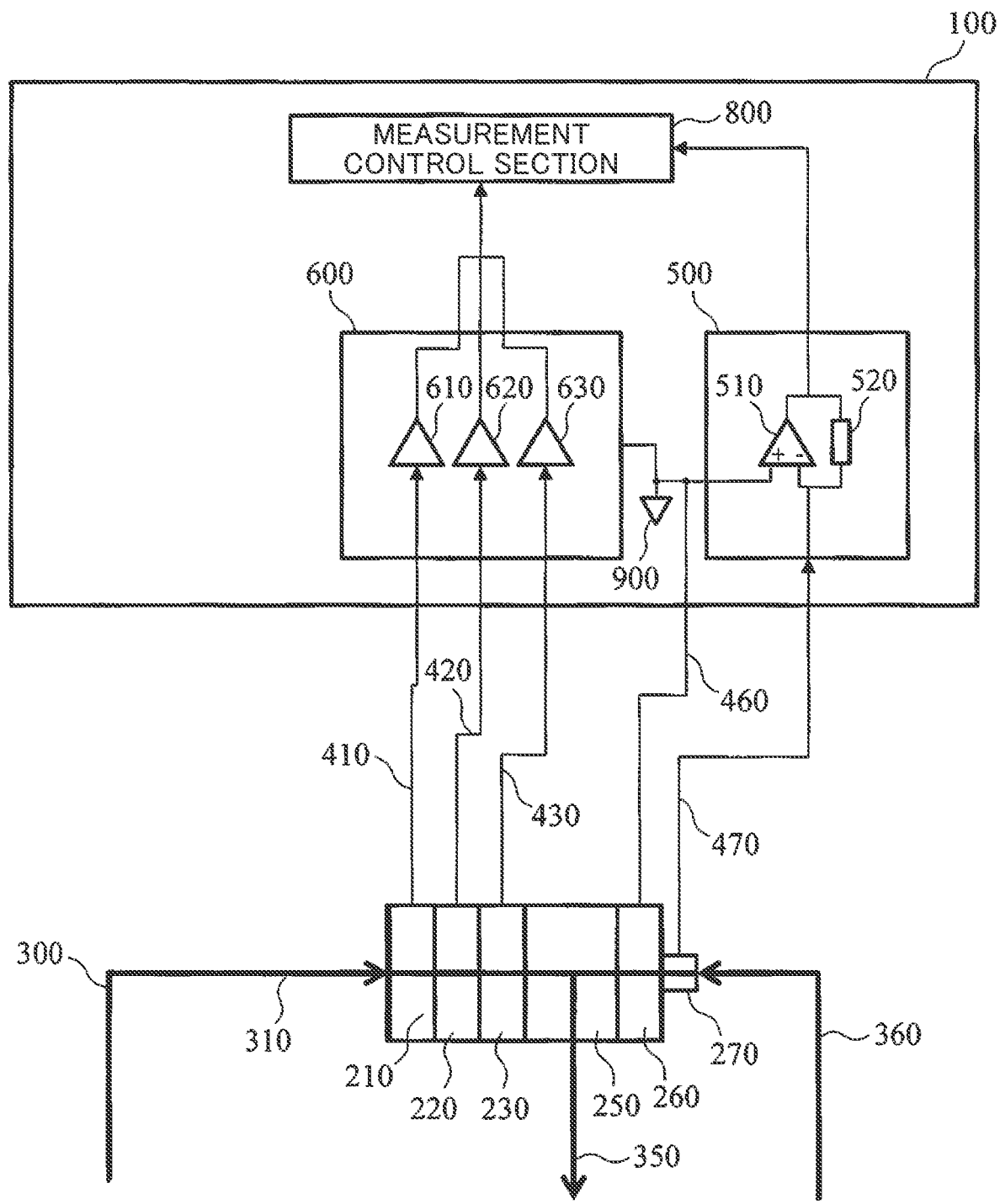
FIG. 11 is a circuit diagram explaining a configuration example of the measurement control device 100 according to the fourth embodiment further in detail.

A fourth embodiment according to the present invention is explained in reference to FIG. 10 and FIG. 11. In the fourth embodiment, the overall configuration (FIG. 1) is the same as the first embodiment. In the fourth embodiment, the configuration of a measurement control device 100 is different from the first embodiment.

An electrolyte measuring device according to the fourth embodiment measures an electric current (hereunder referred to as a "natural electric current") flowing steadily in a reference electrode 260, instead of detecting the presence or absence of air bubbles in a flow channel of a flow cell, as an indicator of failure of the device during the measurement of a diluted specimen liquid similarly to the second embodiment. A measurement control device 100 according to the second embodiment therefore, unlike the first embodiment: excludes a voltage application section 700 and an electric wire 400; and has only a current measurement section 500 and a voltage amplifier 600.

In the device according to the fourth embodiment, an input terminal of a current measurement section 500 is connected to an electrode 270 connected to the rear surface of a reference electrode 260 through a shielded wire 470 similarly to the third embodiment. The fourth embodiment therefore can secure the second embodiment and can make a flow channel of a flow cell longer than the second embodiment in the measurement of a natural electric current.

Fifth Embodiment

Figure 12:
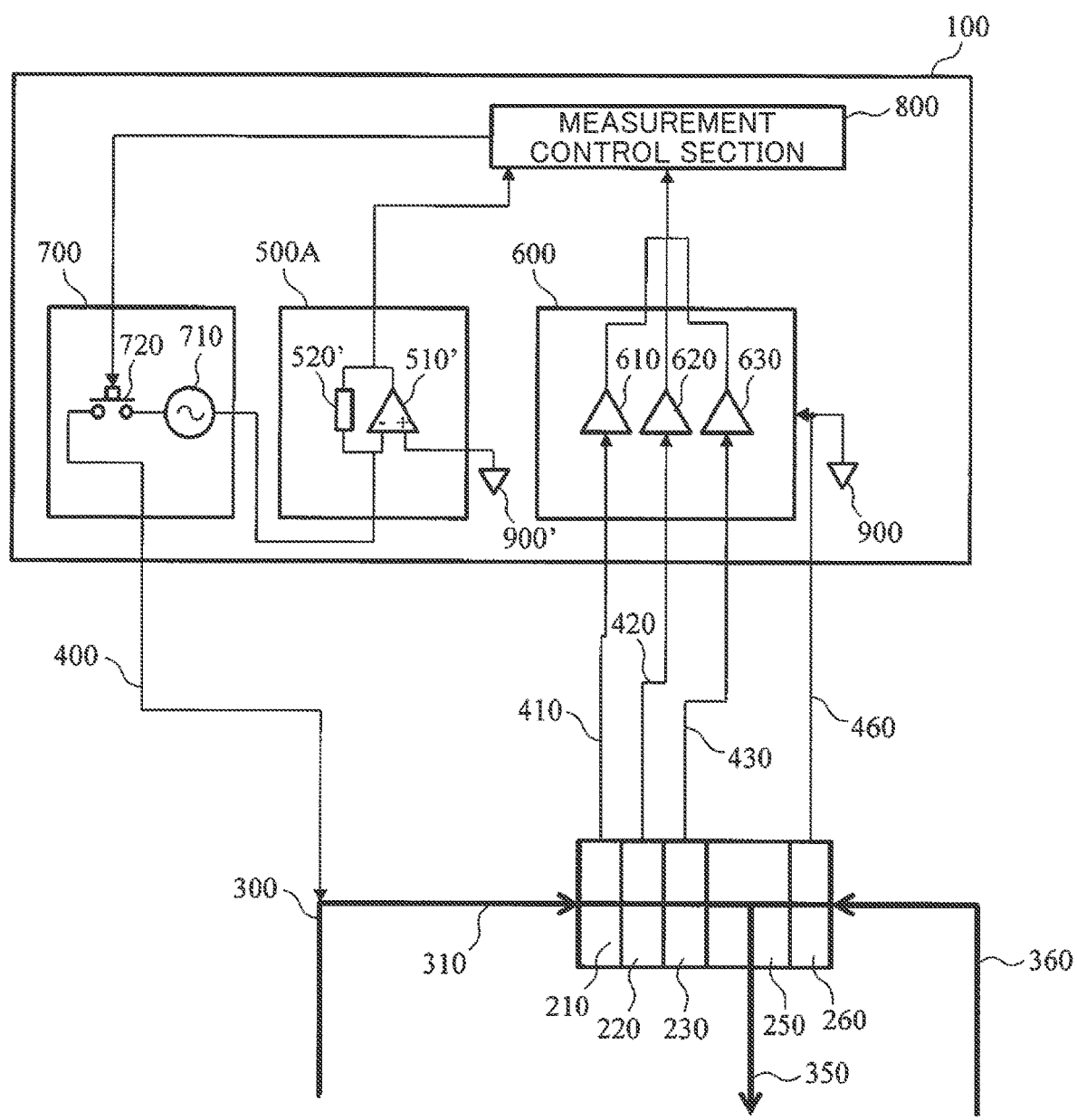
FIG. 12 is a schematic diagram showing a detailed configuration of a measurement control device 100 according to a fifth embodiment together with ambient constituent components.

An electrolyte measuring device according to a fifth embodiment is explained in reference to FIG. 12. In the fifth embodiment, the overall configuration (FIG. 1) is the same as the first embodiment. In the fifth embodiment, the configuration of a measurement control device 100 is different from the first embodiment.

FIG. 12 is a schematic diagram showing a configuration of a measurement control device 100 in an electrolyte measuring device 10 according to the fifth embodiment. In the measurement control device 100, a current measurement section 500A is connected between a power source 710 and a ground terminal 900'. This point is different from the first embodiment in which a current measurement section 500 is connected between a reference electrode 260 and a ground terminal 900. An electric current leading to a flow cell however flows along a loop of passing from a voltage application section 700 through ion-selective electrodes 210 to 230, a liquid junction section 250, a reference electrode 260, and a measurement control section 800 and returning to the voltage application section 700. The current measurement section 500A therefore can measure an electric current flowing in the reference electrode 260 similarly to a current measurement section 500 in the first embodiment.

The current measurement section 500A has an OP amplifier 510' and a feedback resistance 520' similarly to the current measurement section 500 in the first embodiment and the connection relationship between the two is similar to the first embodiment. The power source 710 is connected to an inverted input terminal of the OP amplifier 510' and the ground terminal 900' is connected to a non-inverted input terminal. On the other hand, a shielded wire 460 is not connected to the current measurement section 500A but is connected to a ground terminal 900 in the same manner as before.

In this way, according to the fifth embodiment, an electric current flowing in the reference electrode 260 is measured by using the current measurement section 500. On the other hand, the reference electrode 260 is connected directly to the ground terminal 900 (a configuration similar to a conventional device). In this point, the configuration of a flow cell type ISE is nearly identical to a conventional configuration and hence a high level of compatibility with a conventional device can be maintained.

The present invention is not limited to the aforementioned examples and includes various modified examples. The aforementioned examples are explained in detail in order to explain the present invention in an easy-to-understand manner and the present invention is not necessarily limited to having all the explained configurations. Further, it is also possible to replace a part of a configuration in a certain example with a configuration in another example. Furthermore, it is also possible to add a configuration in a certain example to a configuration in another example. Moreover, it is also possible to add, delete, or replace another configuration to, from, or with a part of a configuration in each example.

The functions of the control device, the measurement control device, and the like stated above may be achieved with software by interpreting and executing a program for achieving each function with a processor. Information in programs and files for achieving each function can be placed in storage devices such as a memory, a hard disk, an SSD (Solid State Drive), and the like or recording media such as an IC card, an SD card, a DVD, and the like. Further, each of the aforementioned configurations or the like may be achieved with hardware by designing a part or the whole of that with an integrated circuit and the like for example.

In the aforementioned embodiments, control lines and information lines indicate what is considered necessary for explanation and not all control lines and information lines are always shown on a product. All the configurations may be interconnected.

LIST OF REFERENCE SIGNS

10 electrolyte measuring device
100 measurement control device
110 dilution tank
120 specimen dispensing mechanism
121 specimen container
130 diluent liquid dispensing mechanism
131 diluent liquid tank
140 internal standard liquid dispensing mechanism
141 internal standard liquid tank
150 liquid feeding mechanism
151 waste liquid container 160 reference electrode liquid feeding mechanism
161 reference electrode liquid tank
170 display section
210, 220, 230 ion-selective electrode
250 liquid junction section
260 reference electrode
270 electrode
300 suction nozzle
310 suction pipe
330 diluent liquid dispensing pipe
340 internal standard liquid dispensing pipe
350 liquid feeding pipe
360 reference electrode liquid feeding pipe
370 waste liquid nozzle
380 waste liquid valve
390 waste liquid mechanism
400 electric wire
410, 420, 430, 460, 470 shielded wire
500, 500A current measurement section
510, 510' OP amplifier
520, 520' feedback resistance
600 voltage amplifier
610, 620, 630 impedance conversion circuit
700 voltage application section
710 power source
720 analog switch
800 measurement control section
900 ground terminal

The invention claimed is:

1. An electrolyte measuring device comprising:
an ion-selective electrode arranged to be placed into contact with an ion solution;
a reference electrode;
a measurement section configured to measure a potential difference between the ion-selective electrode and the reference electrode; and
a current measurement section configured to measure an electric current flowing in the reference electrode as an electric current in a state of not applying a voltage to a flow channel leading from a suction nozzle to the ion-selective electrode and the reference electrode,
wherein an input terminal of the current measurement section is connected to an output terminal of the reference electrode.

2. An electrolyte measuring device according to claim 1, wherein the current measurement section has a current-voltage conversion circuit.

3. An electrolyte measuring device according to claim 1, wherein the current measurement section judges a degree of noise by comparing the electric current with a threshold value and the reliability of measurement of the measurement section is judged on the basis of the judgment result.

4. An electrolyte measuring device according to claim 1, further comprising a judgment section to judge a magnitude of a natural electric current flowing in the reference electrode.

5. An electrolyte measuring device according to claim 1, wherein the current measurement section includes:
an OP amplifier having a first input terminal, a second input terminal, and an output terminal; and
a feedback resistance connected between the first input terminal and the output terminal,
wherein the second input terminal is connected to a ground terminal.

6. An electrolyte measuring device comprising:
an ion-selective electrode arranged to be placed into contact with an ion solution;
a reference electrode;
a measurement section configured to measure a potential difference between the ion-selective electrode and the reference electrode;
a current measurement section configured to measure an electric current flowing in the reference electrode as an electric current in a state of not applying a voltage to a flow channel leading from a suction nozzle to the ion-selective electrode and the reference electrode; and
a voltage application section configured to apply a voltage,
wherein the current measurement section measures a resistance value between the ion-selective electrode and the reference electrode by measuring an electric current flowing from the voltage application section to the reference electrode.

7. An electrolyte measuring device according to claim 6, wherein the voltage application section is configured so as to apply a voltage to a first member that is a member getting in wet contact with the ion solution, and
wherein the current measurement section measures a resistance value between the first member and the reference electrode by measuring an electric current flowing from the voltage application section to the reference electrode through the first member.

8. An electrolyte measuring device according to claim 7, wherein the voltage application section includes:
a power source to supply a first voltage; and
a switch that is placed between the power source and the first member and can be switched between a conductive state and a non-conductive state.

9. An electrolyte measuring device according to claim 8, wherein the switch is switched to the conductive state when a flow channel resistance in a flow channel of the ion solution is measured.

10. An electrolyte measuring device according to claim 9, wherein the switch is switched to the non-conductive state when the ion solution is measured.

11. An electrolyte measuring device comprising:
an ion-selective electrode arranged to be placed into contact with an ion solution;
a first electrode which is a reference electrode;
a measurement section to measure a potential difference between the ion-selective electrode and the reference electrode;
a current measurement section to measure an electric current flowing in the reference electrode; and
a second electrode directly connected to the reference electrode,
wherein the current measurement section is connected to the second electrode though a first electric wire, and
wherein an input terminal of the current measurement section is connected to an output terminal of the reference electrode.

12. An electrolyte measuring device according to claim 11, further comprising a second electric wire to connect the reference electrode and a ground terminal.

* * * * *